United States Patent [19]

Stemmler

[11] Patent Number: 4,650,480

[45] Date of Patent: * Mar. 17, 1987

[54] ABSORPTION PAD FOR HYGIENIC APPLICATIONS AND PROCESS FOR ITS MANUFACTURE

[75] Inventor: Kurt Stemmler, Neuwied, Fed. Rep. of Germany

[73] Assignee: Winkler + Dunnebier Maschinenfabrik und Eisengiesserei GmbH & Co. KG, Neuwied, Fed. Rep. of Germany

[ * ] Notice: The portion of the term of this patent subsequent to Dec. 24, 2002 has been disclaimed.

[21] Appl. No.: 712,846

[22] Filed: Mar. 18, 1985

[30] Foreign Application Priority Data

Apr. 21, 1984 [DE] Fed. Rep. of Germany ....... 3415196

[51] Int. Cl.$^4$ ............................................ A61F 13/16
[52] U.S. Cl. ................. 604/368; 604/385 R; 264/510; 264/518
[58] Field of Search ............... 604/367, 368, 380, 382, 604/358, 385; 264/510, 518; 428/124

[56] References Cited

U.S. PATENT DOCUMENTS

| | | | |
|---|---|---|---|
| 2,024,976 | 12/1935 | Mathey et al. | 604/374 |
| 3,294,090 | 12/1966 | Younger | 604/385.1 |
| 3,547,930 | 12/1970 | Blomquist et al. | 604/385 |
| 3,654,929 | 4/1972 | Nillson et al. | 604/368 |
| 3,812,553 | 5/1974 | Marshall et al. | 264/518 |
| 3,863,296 | 2/1975 | Buell | 264/518 |
| 3,966,858 | 6/1976 | Troy et al. | 264/518 |
| 3,971,379 | 7/1976 | Chatterjee | 604/368 |
| 4,285,343 | 8/1981 | McNair | 604/385 R |
| 4,560,379 | 12/1985 | Stemmler | 604/385 R |

Primary Examiner—John D. Yasko
Attorney, Agent, or Firm—Collard, Roe & Galgano

[57] ABSTRACT

There is provided an absorption pad having a C-shaped cross section and a superabsorbent layer embedded therein, said pad being blunted at its forward and rearward ends in the nature of a truncated pyramid. In a process for the manufacture of the absorption pad, the absorption pad blanks are shaped on a flake wheel and subsequently finished as absorption pads by pressing and folding. Prior to the folding step, a superabsorbent material is applied.

12 Claims, 5 Drawing Figures

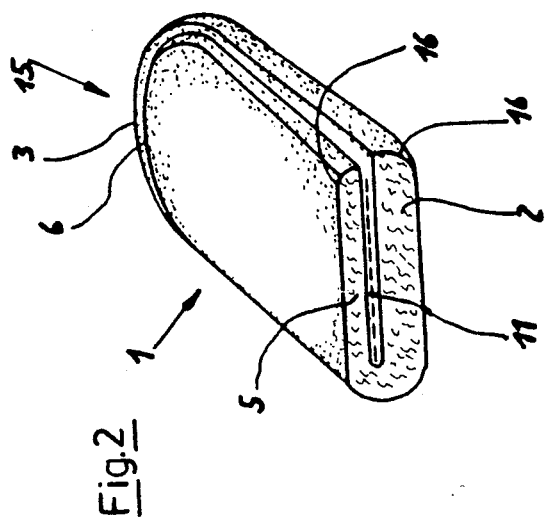
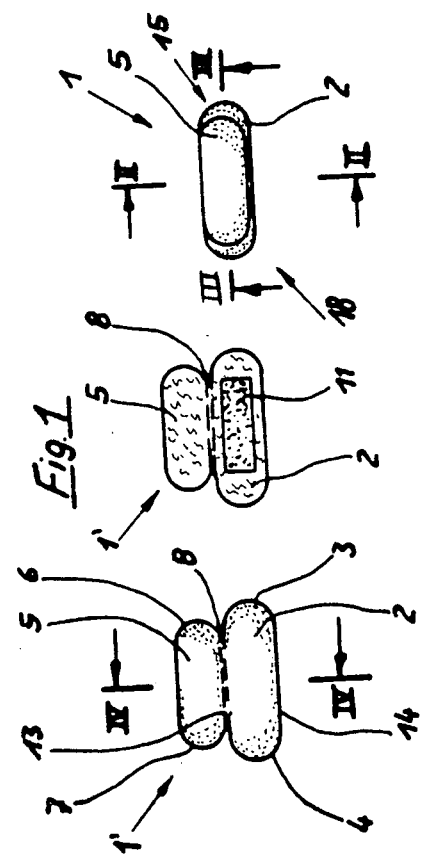
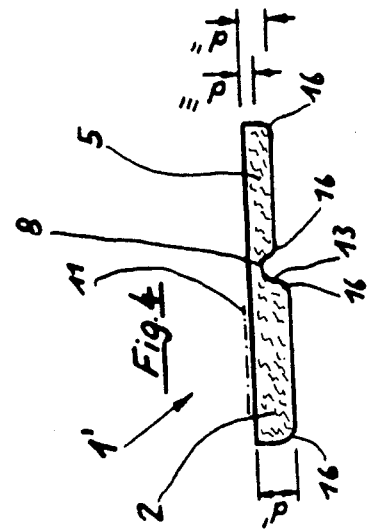
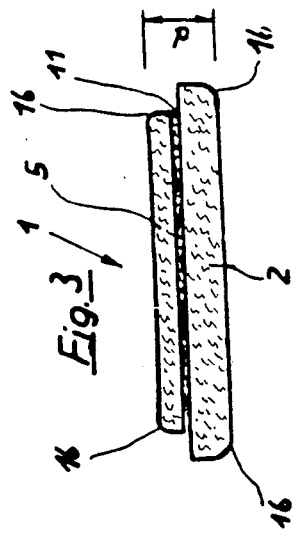

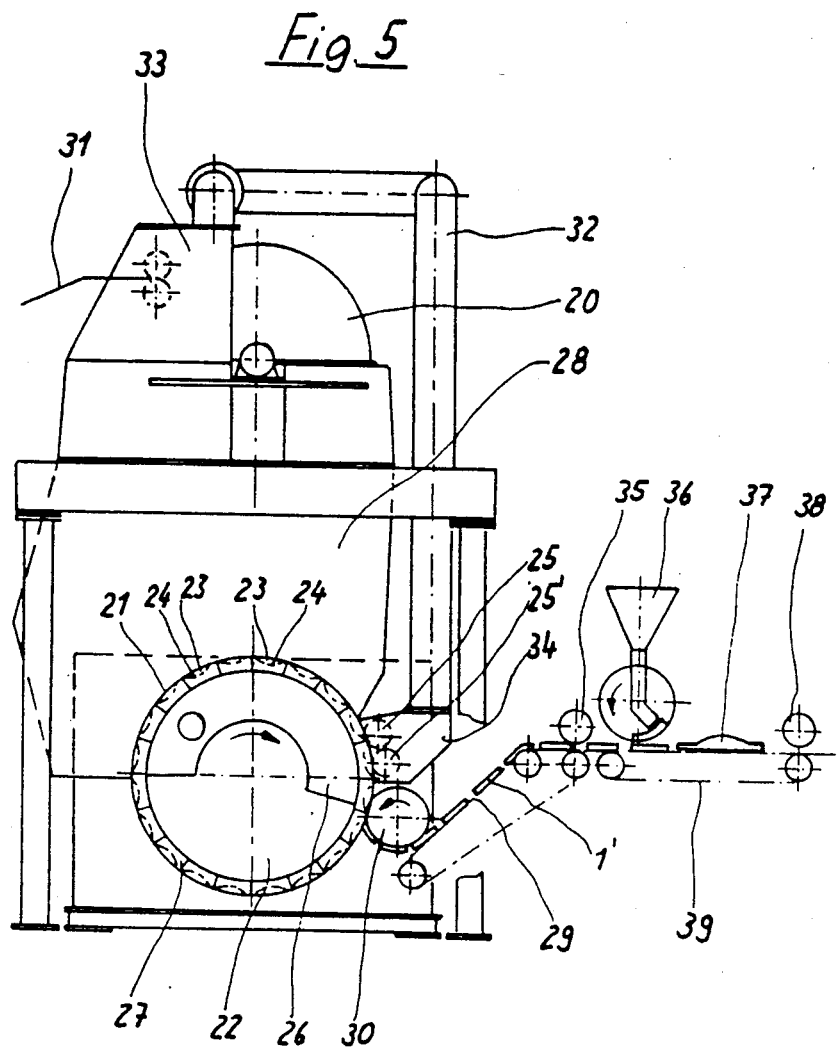

ABSORPTION PAD FOR HYGIENIC APPLICATIONS AND PROCESS FOR ITS MANUFACTURE

The present invention relates to an absorbent pad for hygienic applications such as sanitary napkins, diaper panties and the like, having a two-part flocculent body with a shape conforming to the human body and high absorptivity, and to a process for the manufacture of said absorption pad.

Absorbent pads for hygienic applications are used, for example, in sanitary napkins, slip inserts, disposable diapers and the like. In most cases, such absorption pads are manufactured with the use of hydrophilic cellulose flakes. For increasing the absorptivity and liquid holding capability, an intermediate layer is inserted in the absorption pad in the form of a spread-on layer or strip or band consisting of superabsorbent swelling substances.

In the manufacture of absorption pads for hygienic applications, one object is to provide the absorption pad with sufficient absorptivity for fluids without being excessively voluminous and bulky. Another object is to provide the absorption pad with a fit conforming to the human body in order to increase the wearing comfort thereof. For achieving the first-mentioned object, it has been proposed to increase the absorptivity and liquid-holding capability by using superabsorbent swelling substances embedded in the pad. This proposal has been implemented in a process for the manufacture of absorption pads produced from web-shaped flocculent material. In this process, superabsorbent swelling substances are applied to one half of the web of flocculent material either continuously or in a cycled procedure, and the other half of the web of flocculent material having no superabsorbent substances applied to it is then folded back onto the "coated" half of the web. In this manner, a type of endless sandwich of flocculent material is obtained, which, in a subsequent process step, is separated or divided into individual absorption pads. Absorption pads produced according to this standard process offer poor wearing comfort because they lack a fit which conforms to the human body. Furthermore, such absorption pads have bulky thickenings along their edge as a result of the mechanical cutting during the separation process.

In addition, a process is known in which a multi-part flocculent pad is manufactured by means of shaped cutting of the pad from a relatively thin, but wide web of flaked material. With these flake pads, lateral parts are disposed on an oblong center part without transition, whereby the said lateral parts and said center part have the same geometric shape and size. Said flocculent pads, after having been cut to size, are passed through folding steps, in which the lateral parts are folded over. With said process, a thin flaky web of uniform thickness is produced. Moreover, this type of absorption pad is better adapted to the physical anatomy within the perineal region than the absorption pad previously described. However, due to the cutting of the pad and the long cutting line, unpleasant bulky thickness or material concentration results. Such marginal thickened areas, furthermore, come to rest one on top of the other to some extent when the pad is folded, which causes both the forward and rearward ends of the absorption pad to become bulky to an extent that the wearing comfort of this hygienic article is significantly reduced. Also, the uniform thickness across the total length of the folded absorption pad is not required if such a pad is used in sanitary napkins and disposable diapers, but rather may be a drawback. Since such an absorption pad is stiffer within itself and has unnecessary material accumulations at its ends, it is poorly adapted to the physical shape of the person wearing such a pad. Furthermore, cutting the web of flaky material to size requires continuous removal of the waste in the cutting operation, which, in most cases, is returned to the flaking mill by means of costly vacuum systems. Finally, in the cutting step, substantial amounts of cellulose dust are generated, which soils the machinery and is perceived as a nuisance by the operating personnel.

It is, therefore, an object of the present invention to provide an absorption pad for hygienic applications, which, while having sufficiently high capability for liquid absorption, will not become excessively voluminous and bulky, and which readily adapts itself to the human anatomy in the perineal region. It is also an object of the present invention to provide a process for the manufacture of such an absorption pad.

The above objects, as well as others which will hereinafter become apparent, are accomplished in accordance with the present invention by the provision of an absorption pad for hygienic applications such as sanitary napkins, disposable diapers and the like, having a two-part flocculent body shaped to fit the human body and having high absorptivity. The absorption pad, shaped on a flake wheel with uniform softness also within the zones of its edges, is comprised of an oblong main part with rounded forward and rearward ends and a lateral part arranged on one of the long sides of said main part, the lateral part being shorter than the main part and also rounded on its forward and rearward ends. The lateral part is folded onto the surface of the main part in such a way that a folded absorption pad with a C-shaped cross section is formed, the absorption pad being stepped at its forward and rearward ends in the nature of a truncated pyramid. An intermediate layer is inserted between the pair of adjoining surfaces of the parts folded onto each other, this intermediate layer preferably consisting of a superabsorbent material or flowspreaders.

According to the process for the manufacture of absorption pads as described, a stream of flakes is delivered by a flaking mill, mainly consisting of crushed cellulose, and supplied by means of air to the cylindrical shell of a rotating flake wheel. Over the length of a defined distance, flakes are drawn from the stream of flakes into two-part shaped depressions arranged one after the other in the direction of rotation on the cylindrical shell of the flake wheel. Soft flakes are thus deposited on the sieve-like bottoms of the shaped depressions where, due to compression and felting of the flakes, absorption pad blanks are formed having a lateral part with rounded ends disposed on a long side of an oblong main part with rounded ends, the lateral part being shorter than the main part. Flake material projecting beyond the periphery of the cylindrical shell is removed by brushing and returned to the stream of flakes via a blower. At the end of the vacuum path of the flake wheel, the two-part absorption pad blanks are removed from the shaped depressions of the flake wheel by means of a vacuum roll and delivered to a first conveying line. An intermediate layer, preferably consisting of superabsorbent materials and/or flowspreaders, is applied in portions to selected sections of the main part or to the lateral part of the suction absorption pad blanks. The suction absorption pad blanks are then individually folded one after the other in the direction of transport along their lines of folding in such a way that the lateral part comes to rest on the surface of the main part, forming an absorption pad with a C-shaped cross section. The absorption pads are subsequently compressed.

The advantage achieved by means of the present invention primarily lies in the fact that a process has been developed which permits the continuous shaping of blanks of two-part absorption pads with the help of a rotating flake wheel and the subsequent individual folding of the absorption pads in a way such that absorption pads with a C-shaped cross section are produced. Furthermore, such an absorption pad shaped as defined has the advantage that it has a natural intermediate space in which superabsorbent materials and/or flowspreaders may be inserted for the purpose of enhancing the absorptivity and fluid-holding capability of the pad. In addition, the blank of the absorption pad shaped on the flake wheel has soft marginal zones because no bulky material accumulations are present along the edges as results from a cutting process. Furthermore, due to the fact that the main part and the lateral part have different lengths, an absorption pad is obtained which, after it has been folded with the C-shaped cross section, has a shape stepped in the nature of a truncated pyramid. Such absorption pad readily adapts itself to the anatomy of the perineal region and thus offers high wearing comfort.

Other objects and features of the present invention will become apparent from the following detailed description considered in connection with the accompanying drawings. It is to be understood, however, that the drawings are designed as an illustration only and not as a definition of the limits of the invention.

In the drawings wherein similar reference characters denote similar elements throughout the several views:

FIG. 1 is a schematic representation of the processing of the absorption pad blank to the finished pad, said blank having been shaped on a flake wheel;

FIG. 2 is a perspective cross-sectional view of the finished absorption pad taken along line II—II of FIG. 1;

FIG. 3 is a longitudinal cross-sectional view of the finished absorption pad taken along line III—III of FIG. 1;

FIG. 4 is a cross-sectional view of the absorption pad blank taken along line IV—IV of FIG. 1; and FIG. 5 is a schematic elevational view of the flake wheel with the flaking mill for forming the absorption pad according to the present invention.

Now turning to the drawings, there is shown in FIGS. 1 and 4 an absorption pad blank 1' comprised of the parts 2 and 5 having the thickness d' and d", respectively. Lateral part 5 is arranged on main part 2 which has rounded forward and rearward ends 3 and 4, respectively. Lateral part 5 is shorter and thinner than main part 2 and also rounded at its ends 6 and 7. In a preferred embodiment, thickness d" of lateral part 5 is half the thickness d' of main part 2. A transitional zone 8 having a thickness of d''', being smaller than d', is disposed between main part 2 and lateral part 5, said zone extending along the side 13.

In FIG. 2 there is shown the finished absorption pad 1 having a laminated body with a C-shaped cross section and having a thickness d. This figure shows that lateral part 5 is folded onto or against main part 2. Due to the C-folding of absorption pad 1, a natural intermediate space is created between main part 2 and lateral part 5, in which a layer 11 consisting of a superabsorbent material is inserted.

FIG. 3 shows that after the two parts 2 and 5—which have different lengths—are folded into the C-shape, a finished absorption pad 1 is obtained which, at its ends 15 and 18, is stepped in the manner of a truncated pyramid.

Suction pad blank 1' is rounded at its bottom edges 16 as clearly seen in FIG. 3. Thus, after the C-shaped folding step, the rounded edges 16 of part 5 come to rest upwardly, whereas the rounded edges 16 of part 2 remain facing downwardly.

The process for the manufacture of absorption pad 1 is described in connection with FIG. 5. Therein it is shown that in a flaking mill 33, cellulose flakes are produced from an endless cellulose web 31. With the help of a current of air produced by a blower 20, said flakes are delivered to the cylindrical shell 21 of a rotating flake wheel 27 by means of a large-volume conduit 28. A vacuum box 26 is disposed in the interior, designated 22, of rotating flake wheel 27, the latter having the form of a hollow cylinder. Two-part shaped depressions 23 are arranged on the cylindrical shell 21 having sieve or screen-like bottoms 24 and being in communication air-conductively with the interior 22 of the cylinder.

The cellulose flakes are drawn by vacuum from the stream of flakes into the two-part shaped depressions 23 of the rotating flake wheel 27. Initially, in this operation, finer flakes are deposited on the screen-like bottoms 24. The vacuum applied to the shaped depressions 23 via the vacuum box 26 and the sieve bottoms 24 causes a densification and felting of the drawn-in cellulose flakes, producing the two-part absorption pad blanks 1'.

Following the filling of shaped depressions 23 with flocculent material, a combing device 34 is arranged, by which the flocculent material projecting from shaped depressions 23 beyond cylindrical shell 21 is removed by means of the rotating pronged brushes 25 and 25' and returned to blower 20 by way of a conduit 32 for reuse.

Subsequently, the finished two-part absorption pad blanks 1' are removed from the shaped depressions 23 of rotating flake wheel 27 by means of a vacuum roll 30 and delivered to a transport line 29.

At the end of transport line 29, the absorption pad blanks 1' are compressed in a first compression station 35, where it is possible to densify the main parts 2 and lateral parts 5 to different degrees, i.e., to compact the main part to a different degree as compared to the lateral part. After the compression step, absorption pad blanks 1' are received by a conveyor device 39, which passes said blanks under the applicator device 36, where layers 11 consisting of superabsorbent swelling substances are applied to main parts 2, and then into the folding station 37.

In folding device 37, lateral parts 5 are folded against the surface of main parts 2, forming absorption pads 1 with a C-shaped cross section and the truncated ends 15 and 18. Following the folding step, absorption pads 1 are pressed once more in a second pressing device 38.

While only a single embodiment of the present invention has been shown and described, it will be obvious that many changes and modifications may be made thereunto without departing from the spirit and scope of the invention.

What is claimed is:

1. An absorption pad blank for use in hygienic articles such as sanitary napkins, disposable diapers and the like, formed from a blank having a bifurcated single piece flocculent body shaped to fit the human body and having high absorptivity, wherein the absorption pad blank is shaped on a flake wheel with uniform softness throughout including at its edges, said absorption pad blank comprising an oblong main part with rounded forward and rearward ends, and a lateral part integral with said main part and arranged on one of the long sides thereof, said lateral part having a length less than said main part and also being rounded on its forward and rearward ends, said lateral part being folded onto the surface of said main part to form a folded absorption pad blank with a C-shaped cross section, said absorption pad blank being stepped at its forward and rearward ends in the nature of a truncated pyramid, and an intermediate layer being inserted between the adjoining surfaces of said integral main and lateral parts which are folded onto each other.

2. The absorption pad as defined in claim 1, wherein said intermediate layer comprises superabsorbent material.

3. The absorption pad as defined in claim 1, wherein the thickness of said main part is greater than the thickness of said lateral part.

4. The absorption pad as defined in claim 1, wherein the thickness of said main part is two thirds the thickness of said folded absorption pad.

5. The absorption pad as defined in claim 1, wherein the thickness at the long side of said main part connecting said main part to said lateral part is less than the thickness of said lateral part.

6. The absorption pad as defined in claim 1, wherein said absorption pad has top and bottom edges and as a result of shaping the absorption pad blank on said flake wheel, all of said top and bottom edges of the absorption pad are rounded.

7. The absorption pad as defined in claim 1, wherein the lateral part is folded onto the main part along a folding line zone formed of absorbent material.

8. The absorption suction pad as defined in claim 1, wherein the main part and the lateral part have different material densities.

9. A process for the manufacture of absorption pad blanks, comprising the steps of:

(a) conveying a stream of flakes composed mainly of crushed cellulose, from a flaking mill to the cylindrical shell of a rotating flake wheel, via air conveying means;

(b) drawing flakes from the stream of flakes into two-part shaped depressions arranged one after the other in the direction of rotation on the cylindrical shell of the rotating flake wheel, with fine, soft flakes being initially deposited on sieve-like bottoms of the shaped depressions, and, due to compression and felting of the flakes, forming therein absorption pad blanks having a lateral part with rounded ends disposed on a long side of an oblong main part also with rounded ends, said lateral part being shorter than said main part;

(c) removing flake material projecting beyond the periphery of the cylindrical shell by brushing, and returning said removed flake material to the stream of flakes by a blower;

(d) removing the two-part absorption pad blanks from the shaped depressions of the flake wheel at the end of the vacuum path of the flake wheel by means of a vacuum roll and delivering the removed blanks to a first conveying line;

(e) applying an intermediate layer consisting of superabsorbent materials to selected sections of the main part of the absorption pad blanks;

(f) individually and sequentially folding each blank along its line of folding disposed between said main part and said lateral part, in a way such that the lateral part comes to rest on the surface of the main part to form an absorption pad blank with a substantially C-shaped cross section; and (g) subsequently compressing the absorption pads.

10. The process as defined in claim 9, wherein the intermediate layer of superabsorbent material is applied in portions to selected sections of the lateral part of the absorption pad rather than the main part.

11. The process as defined in claim 9, which further comprises compressing and densifying the main and lateral parts to different degrees prior to the application of superabsorbent materials.

12. The process as defined in claim 10, which further comprises compressing and densifying the main and lateral parts to different degrees prior to the application of superabsorbent materials.

* * * * *